United States Patent [19]

Miyazawa et al.

[11] Patent Number: 4,900,680
[45] Date of Patent: Feb. 13, 1990

[54] METHOD AND APPARATUS FOR MEASURING LIPID PEROXIDE

[75] Inventors: Teruo Miyazawa; Keiichi Yasuda; Kenshiro Fujimoto; Akio Saeki, all of Sendai, Japan

[73] Assignee: Tohoku Electronic Industrial Co., Ltd., Sendai, Japan

[21] Appl. No.: 167,817

[22] Filed: Mar. 14, 1988

[30] Foreign Application Priority Data

Mar. 20, 1987 [JP] Japan .................................. 62-67242

[51] Int. Cl.⁴ .......................................... G01N 33/92
[52] U.S. Cl. ........................................ 436/71; 422/70
[58] Field of Search .................. 435/25, 28, 192, 810, 435/26, 931, 4, 184; 422/70; 436/71, 13; 73/61 C

[56] References Cited

U.S. PATENT DOCUMENTS 4,367,285  1/1983  Yamaguchi et al. .................. 435/28
4,657,856  4/1987  Terada et al. ......................... 435/28
4,675,281  6/1987  Lands et al. .......................... 435/4

OTHER PUBLICATIONS

Von G. D. Mendenhall, "Analytische Anwendungen der Chemilumineszenz", Angew Chem. 89, 220–228 (1977).

Primary Examiner—Barry S. Richman
Assistant Examiner—T. J. Wallen
Attorney, Agent, or Firm—Reed Smith Shaw & McClay

[57] ABSTRACT

A method and apparatus for measuring a lipid peroxide, in which a sample containing lipids is subjected to a liquid chromatography to separate the lipids into lipid classes. The lipid classes are brought into contact with a luminescent reagent which specifically reacts with a lipid hydroperoxide contained in the lipid classes to generate a light in an amount corresponding to a content of the hydroperoxide. The light is optically detected by a photodetector.

9 Claims, 5 Drawing Sheets

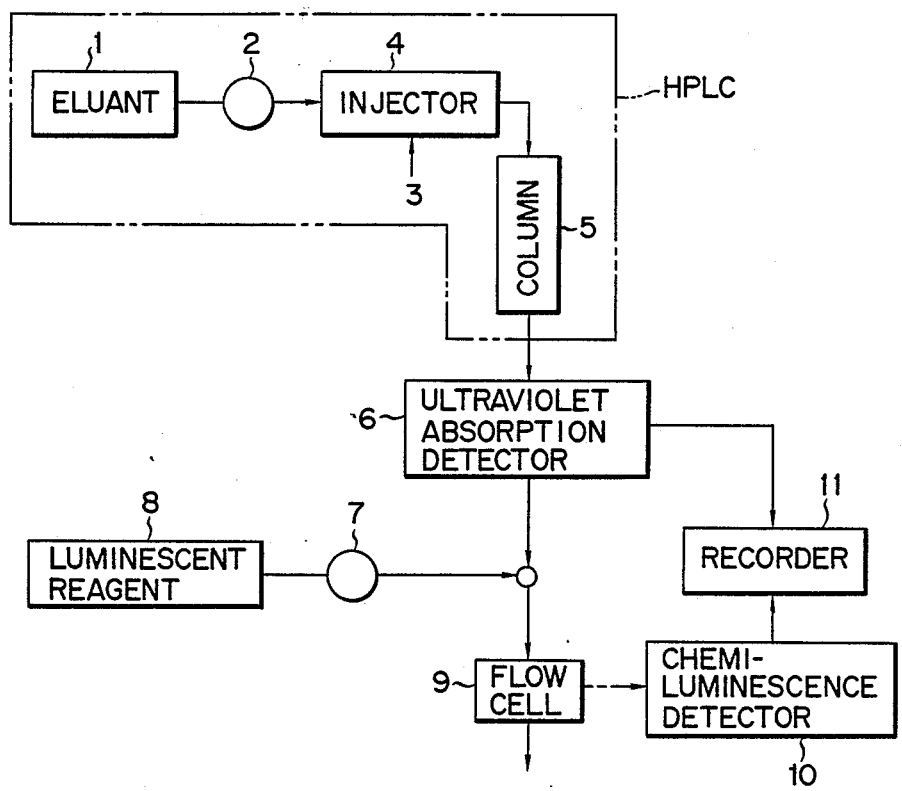
F I G. 1
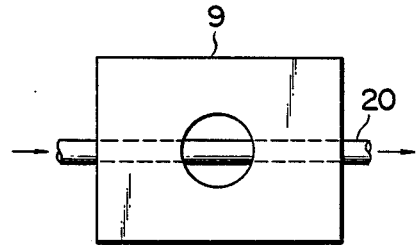
F I G. 2
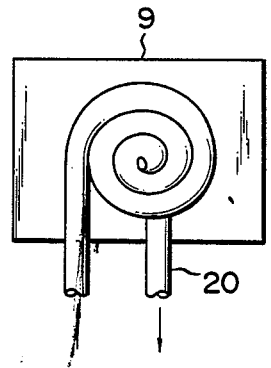
F I G. 3

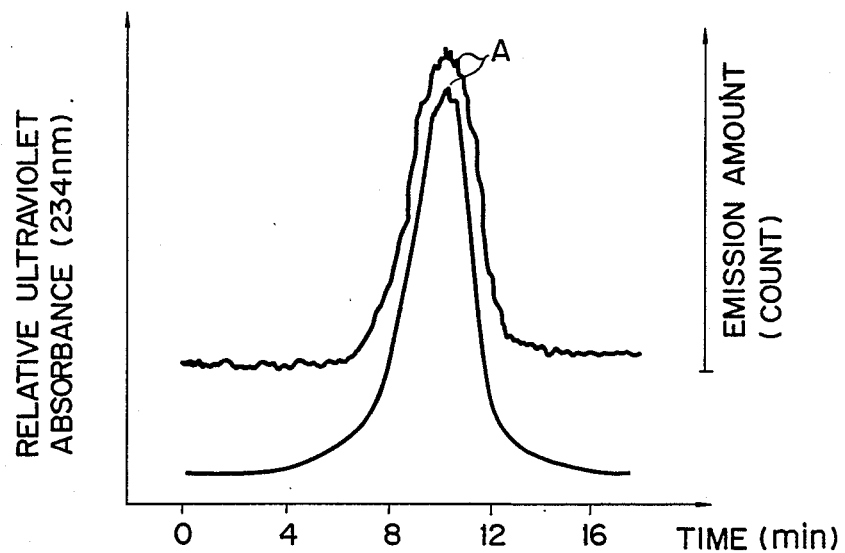
F I G. 4
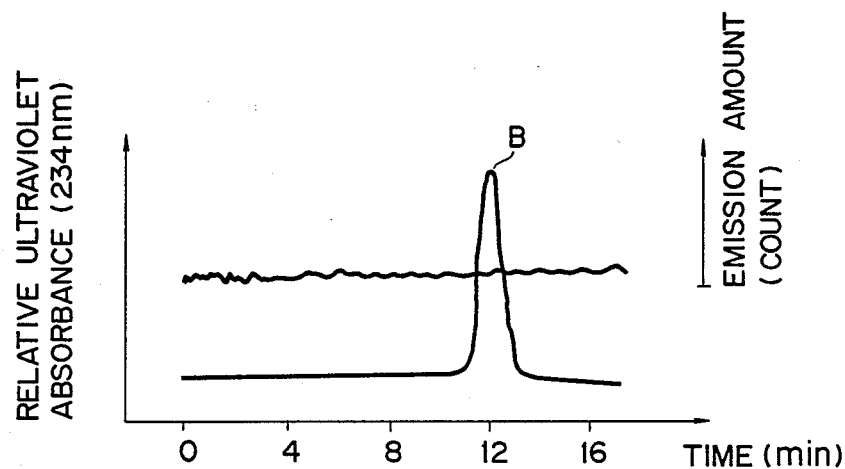
F I G. 5

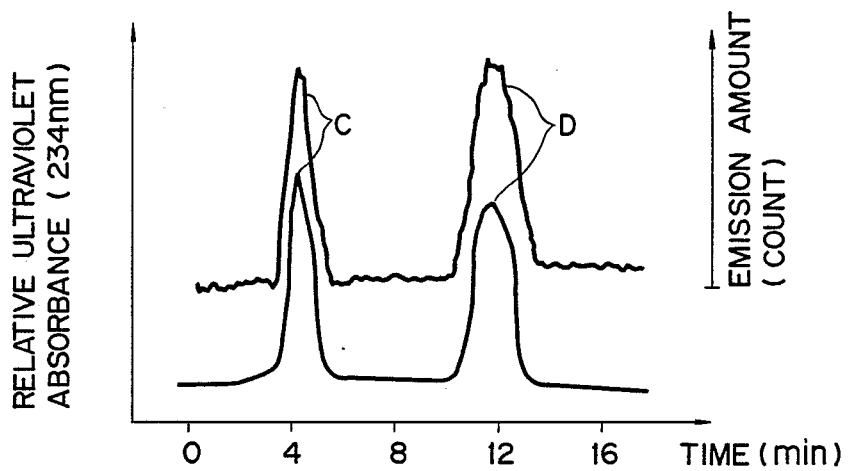
F I G. 6
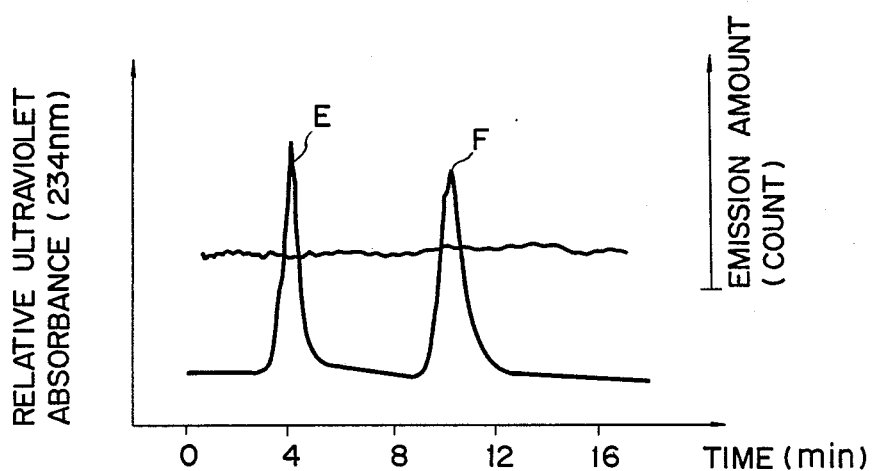
F I G. 7

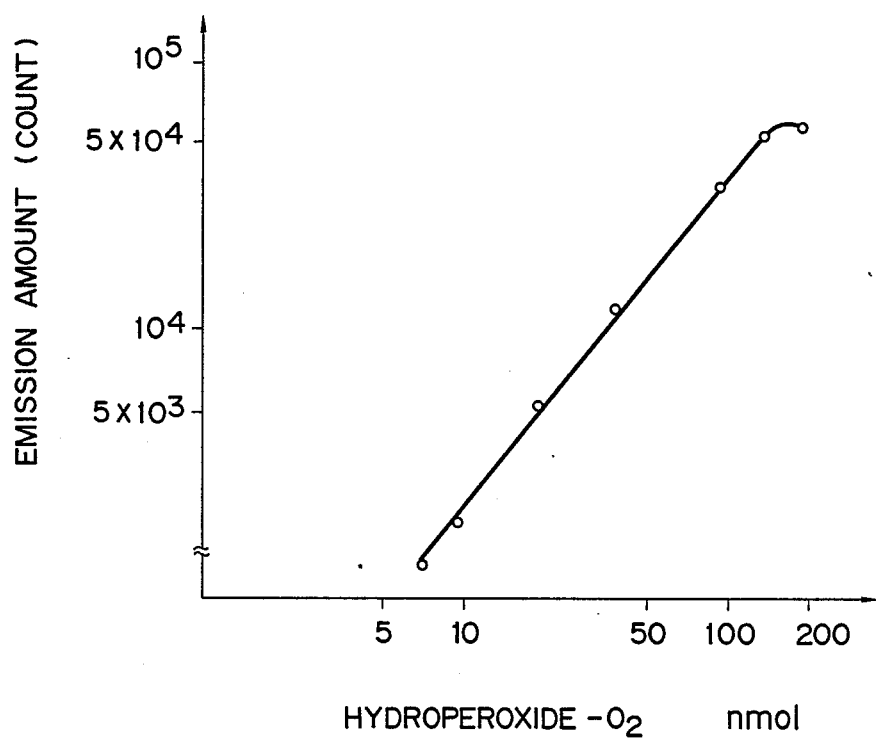
F I G. 8

METHOD AND APPARATUS FOR MEASURING LIPID PEROXIDE

BACKGROUND OF THE INVENTION

1. Field of the Invention

The present invention relates to a method and apparatus for measuring a lipid hydroperoxide at a lipid class level.

2. Description of the Related Art

Lipid peroxides are generally produced when molecular oxygen, active oxygen, or a free radical acts on an unsaturated fatty acid. The unsaturated fatty acid is oxidized by introducing oxygen molecules into double bonds. This oxidation reaction is called autoxidation. When this peroxidation reaction occurs, a cis type double bond site is converted into a conjugated double bond. Therefore, a hydroperoxide type lipid peroxide having a conjugated double bond is produced.

Oxygen molecules are directly introduced into saturated and unsaturated fatty acids in a photosensitized oxidation reaction. In this case, lipid hydroperoxides with and without a conjugated double bond are produced. A lipid hydroperoxide as a primary product derived by oxidation produces secondary oxides in decomposition and polymerization reactions.

Analysis of lipid peroxides in food and biological samples is based on colorimetry of hydroperoxides in total lipids or of secondary oxidation products. However, lipids have different properties and functions. In order to examine the existing forms and physiological meanings of lipids in food and living organisms or study a detailed mechanism of lipid oxidation, lipid peroxide levels must be analyzed in units of lipid classes (e.g., phosphatidylcholine hydroperoxide and phosphatidylethanolamine hydroperoxide as phospholipid classes).

The phospholipid is a component of a membrane of a living organism and is most important as a functional lipid for forming a micell with protein. The phospholipid easily changes since it contains large amounts of highly unsaturated fatty acids such as an arachidonic acid. The arachidonic acid serves as a precursor of many physiological active materials, e.g., as a precursor of prostanoids which exhibit strong hormonic effects. It is very important to analyze hydroperoxides of phospholipids containing large amounts of arachidonic acid for studying various diseases and geriatric diseases. Therefore, a strong demand has arisen for establishing a method of fractionation measurement of an amount of a hydroperoxide of, e.g., a glycerophospholipid including phosphatidylcholine as a main phospholipid.

In a conventional high performance liquid chromatography (HPLC)-ultraviolet absorption method, a hydroperoxide and a hydroxy derivative as its reduced product have the same retention time and the same peak (234 nm) of conjugated diene. It is therefore difficult to discriminate the hydroperoxide from its reduced product, a hydroxy derivative, and hence to accurately measure the hydroperoxide. In addition, the ultraviolet absorption method is adversely affected by an unoxidized lipid.

SUMMARY OF THE INVENTION

The present invention is mainly directed to solve a problem posed by the fact that a hydroperoxide and its hydroxy derivative have the same retention time and the same absorption peak to cause a difficulty in measuring only the hydroperoxide.

It is an object of the present invention to provide a method and apparatus for measuring a lipid peroxide in which a lipid sample is separated into lipid class levels, and a lipid hydroperoxide contained in the lipid classes is accurately measured.

A method according to the present invention comprises the steps of: separating a lipid sample into each of lipid classes by liquid chromatography; mixing a luminescent reagent with each of the separated lipid classes, thereby reacting the luminescent reagent with a lipid hydroperoxide contained in the lipid class; and optically measuring light produced by the reaction by a photodetecting means.

An apparatus according to the present invention comprises: liquid chromatography means for separating a sample into lipid classes; mixing means for mixing a luminescent reagent with each of the separated lipid classes to react the luminescent reagent with a lipid hydroperoxide contained in the lipid class; and photodetecting means for detecting light produced by the reaction.

According to the present invention, the sample is separated into the lipid classes by liquid chromatography, the luminescent reagent is mixed with the separated lipid class. The luminescent reagent reacts specifically with the lipid hydroperoxide if present in the lipid class, and emits light corresponding to the amount of the hydroperoxide contained in the classified lipid detected by the photodetecting means. Therefore, the hydroperoxide in each of the lipid classes can be accurately measured by detecting the emitted light.

BRIEF DESCRIPTION OF THE DRAWINGS

FIG. 1 is a view showing an apparatus for measuring a lipid peroxide according to an embodiment of the present invention;

FIGS. 2 and 3 are plan views showing flow cells, respectively;

FIGS. 4 to 7 are graphs showing measurement results;

FIG. 8 is a graph showing a detected emission amount; and

DETAILED DESCRIPTION OF THE PREFERRED EMBODIMENTS

Figure 9:
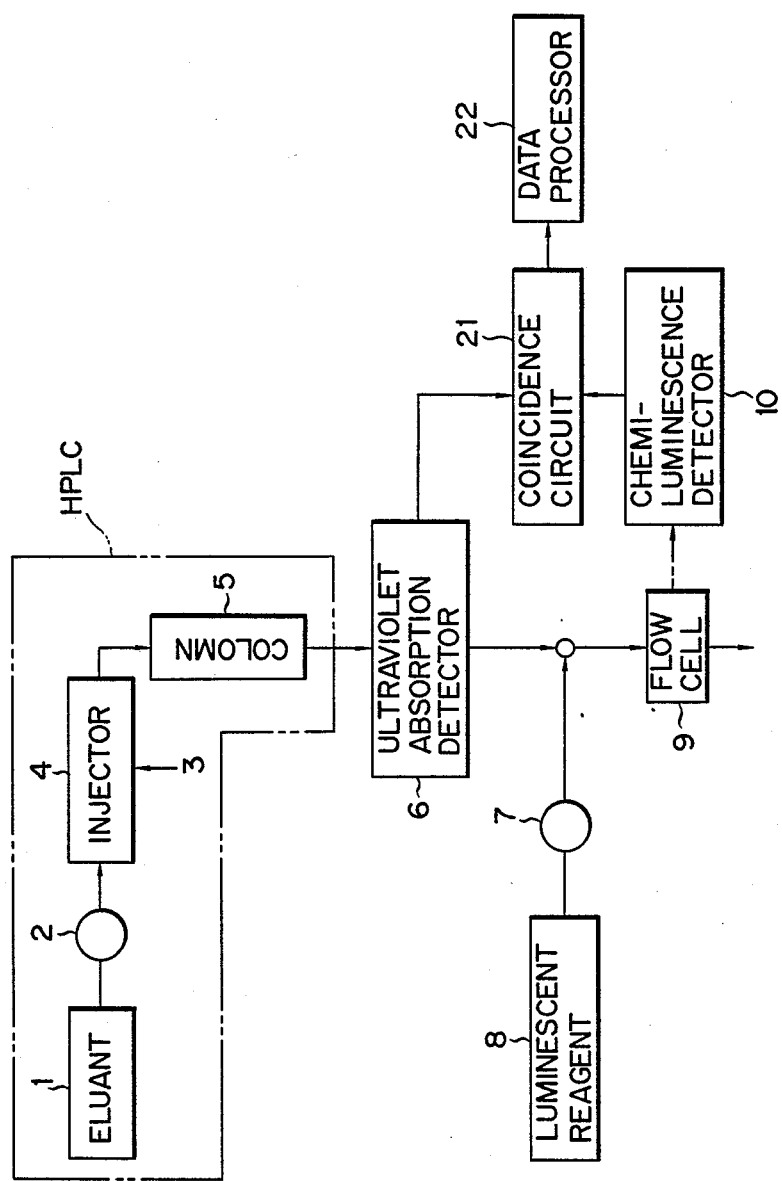
FIG. 9 is a view showing an apparatus for measuring a lipid peroxide according to another embodiment of the present invention.

The present invention combines a liquid chromatography with an emission spectroanalysis utilizing a luminescent reagent which specifically reacts with a lipid hydroperoxide to analyze the hydroperoxide. Lipid hydroperoxides in a very small amount, e.g., on the order of nmols contained in several to several tens of microliters of a sample is separated into lipid class levels and can be easily measured.

Briefly, a sample is fed to a high performance liquid chromatography. Each class of compounds separated by the liquid chromatography is monitored by an ultraviolet absorption detector, and at the same time a hydroperoxide in each monitored peak is reacted with a salt or hydroxide of a transition metal which produces a cation having a valency of 2, a complex of a transition metal having a valency of 2, a heme, a heme peptide, a heme protein, or a heme enzyme. The resultant active oxygen and oxygen radicals react with a luminescent substance, and light emitted by this reaction is optically measured.

FIG. 1 shows a measuring apparatus according to an embodiment of the present invention.

Referring to FIG. 1, high performance liquid chromatography (HPLC) comprises liquid feed pump 2 for feeding elution solvent 1, injector 4 for injecting sample 3 into the fed elution solvent (eluant), and column 5 for receiving the elution solvent mixed with the sample fed by injector 4. Ultraviolet absorption detector 6 is arranged at an elution portion of column 5 to detect ultraviolet absorption of each component eluted according to an adsorption capacity of an adsorbent in column 5. A luminescent reagent 8 is injected by liquid feed pump 7 into each of the components passing through ultraviolet absorption detector 6. Each component injected with the luminescent reagent 8 is supplied to flow cell 9. A photoelectron multiplier of chemiluminescence detector 10 of a single photoelectron count type opposes flow cell 9. Chemiluminescence detector 10 detects light from each component passing through flow cell 9. Detection results of chemiluminescence detector 10 and ultraviolet absorption detector 6 are recorded by recorder 11 comprising, e.g., a pen recorder.

Flow cell 9 has an internal volume of, for example, about 60 microliters and is made of a quartz glass tube or transparent Teflon tube.

FIGS. 2 and 3 show structures of flow cell 9. The flow cell in FIG. 2 has linear tube 20, while the flow cell in FIG. 3 has spiral tube 20. Although the straight tube has low detection sensitivity, it has high peak resolution. To the contrary, the spiral tube has good detection sensitivity, but it has low peak resolution.

Examples of the absorbent in column 5 in HPLC are chemically bonded silica gel, hydrophillic polymer gel, silica gel, polysaccharide gel, polystyrene gel, a polystyrene gel derivative, and a polysaccharide gel derivative. Column 5 is preferably an ODS (octadecylsilane)-treated reverse phase column treated with octadecylsilane or a normal phase silica gel column.

Examples of a catalyst acting on a lipid hydroperoxide to produce active oxygen species such as active oxygen or oxygen radicals are: a transition metal salt which produces a cation having a valency of 2 (e.g., ferrous chloride, ferrous sulfate, potassium ferricyanide, each of which produces $Fe^{2+}$; manganous chloride or manganous sulfate, each of which produces $Mn^{2+}$; or cobalt chloride or cobalt sulfate, each of which produces $Co^{2+}$); a hydroxide of the transition metals described above; a complex of a transition metal having a valency of 2 (e.g., $Fe^{II}$-porphyrin complex); a heme protein (e.g., cytochrome C, hemoglobin, or myoglobin); a heme peptide (e.g., a compound obtained by decomposing a heme protein by a protease such as chymotrypsin or trypsin); and a heme enzyme (e.g., horseradish peroxidase or prostaglandin peroxidase).

A preferable catalyst compound is a heme protein, a heme peptide, or a heme enzyme. Most usually, the heme protein such as cytochrome C is used due to easy handling. The concentration of the catalyst compound can fall within the range of 0.1 $\mu$g/ml to 1,000 $\mu$g/ml and usually falls within the range of 1 $\mu$g/ml to 200 $\mu$g/ml. For example, best luminous efficiency can be obtained when the concentration is about 10 $\mu$g/ml for cytochrome C, about 120 $\mu$g/ml for cytochrome C heme peptide; and about 10 $\mu$g/ml for horseradish peroxidase.

The luminescent substance is not limited to a specific one, provided it reacts with active oxygen or an oxygen radical to emit light. Examples of such a compound are: polyhydroxyphenols (e.g., pyrogallol and perprogalline); a phthaladine derivative (e.g., luminol or isoluminol); an indol derivative (e.g., indoleacetic acid, skatole, or tryptophan); a thiazolidine derivative (e.g., Cypridinacea luciferin or lophine); an acrydine derivative (e.g., lucigenine), an oxalic acid derivative (e.g., bistrichlorophenyloxalate); and a 1,2- dioxa-4,5-azine derivative. The concentration of the luminescent substance varies depending on the compound used. The concentration is preferably 0.1 $\mu$g/ml or more. When luminol is used, its concentration is most preferably 1 $\mu$g/ml.

Examples of the lipid hydroperoxide to be detected are a hydroperoxide of a saturated fatty acid (e.g., palmitic acid hydroperoxide, stearic acid hydroperoxide, and their ester derivatives); a hydroperoxide of an unsaturated fatty acid (e.g., oleic acid hydroperoxide, linoleic acid hydroperoxide, linolenic acid hydroperoxide, arachidonic acid hydroperoxide, and their ester derivatives); a hydroperoxide of a glycerolipid (e.g., triacylglycerol hydroperoxide, glycerophospholipid hydroperoxide, glyceroglycolipid hydroperoxide); a hydroperoxide derived from food or a living organism component (e.g., a hydroperoxide derived from a serum lipid or edible oil or fat, a hydroperoxide derived from a lipoprotein, and a hydroperoxide contained in biotissue or fish or animal meat).

When the above measuring apparatus is used, measurement is preferably performed in a weak basic solution of a luminescent reagent such as a heme protein and luminol. When the reagent solution has a pH value of 9 to 10, good results can be obtained. A buffer for providing the above properties is a borate buffer ($H_3BO_3$—KOH), a carbonate buffer ($Na_2CO_3$—$NaHCO_3$), a glycine buffer ($NH_2CH_2COOH$—NaOH), or the like. The borate buffer is most preferable.

In order to prevent oxygen dissolved in the luminescent reagent solution from interfering analysis of a very small amount of hydroperoxide, the luminescent reagent solution is desirably purged with an inert gas to remove oxygen to obtain a stable measurement value. Examples of the inert gas are nitrogen gas and argon gas.

The concentration of the lipid hydroperoxide in lipid sample is calculated based on a calibration curve. The calibration curve can be formed by using a material selected from methyl linolate hydroperoxide, arachidonic acid hydroperoxide, phosphatidylcholine hydroperoxide, phosphatidylethanolamine hydroperoxide, and triacylglycerol hydroperoxide.

The present invention will be described in more detail by way of examples below.

A measurement sample was a phosphatidylcholine hydroperoxide prepared by photosensitized oxidation of egg-yolk phosphatidylcholine, using methylene blue.
Column Elution Solvent:
Chloroform-methanol (1: 9 V/V (volume ratio); flow rate: 1.1 ml/min)
Column Elution Solvent Feed Pump 2: 880-PU pump available from Nihon Bunko K.K.
Sample Injector 4: VMD-EIE sample injector available from Shimamura Keiki Seisaku-Sho
Column 5: TSK-Gel silica 60 column (5 $\mu$m, 250 $\times$ 4.6 mm) available from Toyo Soda Kogyo K.K.
Ultraviolet Absorption Detector: UVIDEC-100-III UV detector available from Nihon Bunko K.K.

Luminescent Reagent: 50 mM Borate buffer (pH 9.3) dissolving cytochrome C (1 μg/ml) and luminol (10 μg/ml)

Luminescent Reagent Liquid Feed Pump 7: KHD-52 pump available from Kyowa Seimitsu K.K.

Chemiluminescence Detector: Chemiluminescence analyzer OX-7 available from Tohoku Denshi Sangyo K.K.

Recorder 11: SEKONIK SS-250F 2-pen recorder

FIG. 4 shows analysis results of phosphatidylcholine hydroperoxide (PCOOH) as a sample by using the measuring apparatus described above. Peaks A of PCOOH are detected on a chromatogram by ultraviolet absorption detector 6 and chemiluminescence detector 10.

FIG. 5 is a graph showing an analysis result when hydroxyphosphatidyl choline (PCOH) obtained by reducing PCOOH by sodium borohydride is used as a sample. Peak B detected by ultraviolet absorption detector 6 is not detected by chemiluminescence detector 10. By utilizing chemiluminescence detector 10, only the hydroperoxide can be specifically detected. This peroxide cannot be distinguished by ultraviolet absorption detector 6.

FIG. 6 shows a chromatogram when a mixture of PCOOH and phosphatidylethanolamine hydroperoxide (PEOOH) is used as a sample. Peak D of the PCOOH can be properly separated from peak C of the PEOOH. These peaks are detected by chemiluminescence detector 10. Therefore, when a phospholipid sample is analyzed, each of the hydroperoxides in the sample can be separately and specifically detected and differentiated from each other.

FIG. 7 shows a chromatogram when a mixture of unoxidized phosphatidylcholine (PC) and unoxidized phosphatidylethanolamine (PE) is used as a sample. Peak E corresponds to unoxidized PE, and peak F corresponds to unoxidized PC. As is apparent from FIG. 7, the unoxidized lipids are not detected by chemiluminescence detector 10 at all. Note that ultraviolet absorption detector 6 also detects undesirably the unoxidized lipids, and peaks E and F appear on the chromatogram.

According to the measuring method using the above measuring apparatus, lipid hydroperoxides can be specifically detected and measured.

FIG. 8 shows a calibration curve for measuring an amount of PCOOH by the measuring apparatus of the invention. Referring to FIG. 8, the emission amount corresponding to the peak area is plotted along the ordinate, and the concentration of the PCOOH is plotted along the abscissa. The concentration of the PCOOH is proportional to the emission amount in the range of 7 nmol of hydroperoxide-$O_2$ to 140 nmol of hydroperoxide-$O_2$. A minimum detection amount of PCOOH is 7 nmol of hydroperoxide-$O_2$.

FIG. 9 shows a measuring apparatus according to another embodiment of the present invention. The same reference numerals as in FIG. 1 denote the same parts in FIG. 9, and only different parts will be described below.

In this embodiment, detection output signals from ultraviolet absorption detector 6 and chemiluminescence detector 10 are supplied to coincidence circuit 21. Coincidence circuit 21 compares a detection result of ultraviolet absorption detector 6 with a detection result of chemiluminescence detector 10, i.e., peak positions detected by detectors 6 and 10. A detection result is supplied to data processor 22 comprising a microcomputer or the like. When a coincidence output is generated by coincidence circuit 21, the microcomputer determines that the lipid hydroperoxide has been detected, and a measurement result can be displayed and easily checked.

Since the lipid hydroperoxide can be specifically detected by chemiluminescence detector 10, ultraviolet absorption detector 6 need not always be used. Detector 6 may be used as needed.

Various changes and modifications may be made within the spirit and scope of the invention.

According to the present invention as described above, a lipid sample is separated into lipid classes by a liquid chromatography. A luminescent reagent is mixed with each of the lipid classes and reacted with the lipid hydroperoxide to emit light. The separated hydroperoxide can be detected by a photodetecting means. Therefore, the lipid hydroperoxide contained in the lipid classes can be accurately and properly measured.

What is claimed is:

1. A method of detecting a lipid hydroperoxide, comprising:
   subjecting a sample containing lipids to a liquid chromatography to separate the lipids into lipid classes;
   bringing the lipid classes into contact with a luminescent reagent which specifically reacts with lipid hydroperoxide contained in the lipid classes to generate a light in an amount corresponding to a content of the hydroperoxide; and
   optically detecting said light by photodetecting means.

2. A method according to claim 1, wherein said liquid chromatography comprises high performance liquid chromatography.

3. A method according to claim 1, wherein said photodetecting means comprises a chemiluminescence detector.

4. A method according to claim 1, wherein said luminescent reagent comprises a catalyst which acts on the hydroperoxide to produce active oxygen species and a luminescent substance which reacts with the active oxygen species to emit the light.

5. A method according to claim 4, wherein said catalyst is a material selected from the group consisting of a heme protein, heme peptide, and heme enzyme.

6. A method according to claim 1, wherein said sample has a pH value of 9 to 10.

7. A method according to claim 1, wherein oxygen is eliminated from said sample.

8. A method of detecting a lipid hydroperoxide, comprising:
   a. subjecting a sample containing lipids to a liquid chromatography to separate the lipids into lipid classes;
   b. bringing the lipid classes into contact with a luminescent reagent which specifically reacts with a lipid hydroperoxide contain ⓡin the lipid classes to generate a light in an amount corresponding to a content of the hydroperoxide;
   c. optically detecting said light by photodetecting means;
   d. said luminescent reagent including a catalyst that acts on the hydroperoxide to produce active oxygen species, and a luminescent substance which reacts with the active oxygen species to emit light; and
   e. said catalyst including a material selected from a group consisting of a heme protein, heme peptide, and heme enzyme.

9. A method according to claim 8, wherein said luminescent substance comprises luminol.

* * * * *